US012678588B2

(12) United States Patent
Farrell et al.

(10) Patent No.: US 12,678,588 B2
(45) Date of Patent: Jul. 14, 2026

(54) PACKAGED HYDROPHILIC MEDICAL PRODUCTS THAT ARE HYDRATED WITHIN THE PACKAGE AND METHODS OF MAKING THE SAME

(71) Applicant: Hollister Incorporated, Libertyville, IL (US)

(72) Inventors: David J. Farrell, Ballina (IE); Horacio Montes De Oca, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 1097 days.

(21) Appl. No.: 17/612,964

(22) PCT Filed: May 21, 2020

(86) PCT No.: PCT/US2020/034036
§ 371 (c)(1),
(2) Date: Nov. 19, 2021

(87) PCT Pub. No.: WO2020/237073
PCT Pub. Date: Nov. 26, 2020

(65) Prior Publication Data
US 2022/0233808 A1 Jul. 28, 2022

Related U.S. Application Data

(60) Provisional application No. 62/851,376, filed on May 22, 2019.

(51) Int. Cl.
| | |
|---|---|
| *A61M 25/00* | (2006.01) |
| *A61L 2/081* | (2026.01) |
| *A61L 2/087* | (2026.01) |
| *A61L 29/08* | (2006.01) |
| *A61L 29/14* | (2006.01) |
| *A61L 103/15* | (2026.01) |

(52) U.S. Cl.
CPC ........... *A61M 25/002* (2013.01); *A61L 2/081* (2013.01); *A61L 2/087* (2013.01); *A61L 29/085* (2013.01); *A61L 29/14* (2013.01); *A61L 2103/15* (2026.01); *A61L 2202/18* (2013.01); *A61L 2400/10* (2013.01); *A61L 2430/22* (2013.01); *A61M 2025/0046* (2013.01); *A61M 2210/1096* (2013.01)

(58) Field of Classification Search
None
See application file for complete search history.

(56) References Cited

U.S. PATENT DOCUMENTS

| | | | |
|---|---|---|---|
| 6,409,717 | B1 | 6/2002 | Israelsson et al. |
| 7,066,912 | B2 | 6/2006 | Nestenborg et al. |
| 7,476,223 | B2 | 1/2009 | McBride |

(Continued)

FOREIGN PATENT DOCUMENTS

| | | |
|---|---|---|
| EP | 2295108 A1 | 3/2011 |
| WO | 2018156502 A2 | 8/2018 |

OTHER PUBLICATIONS

International Search Report and Written Opinion Dated Jul. 14, 2020 for International Application No. PCT/US2020/034036.

*Primary Examiner* — Lore R Jarrett
(74) *Attorney, Agent, or Firm* — Cook Alex Ltd.

(57) ABSTRACT

Ready to use packaged medical products that include hydrated hydrophilic medical devices and methods of making the same.

20 Claims, 1 Drawing Sheet

(56)                    References Cited

U.S. PATENT DOCUMENTS

| | | | |
|---|---|---|---|
| 8,002,766 | B2 | 8/2011 | Tanghoej et al. |
| 8,523,843 | B2 | 9/2013 | Kavanagh et al. |
| 8,740,863 | B2 | 6/2014 | Nestenborg et al. |
| 9,072,862 | B2 | 7/2015 | Murray et al. |
| 11,338,109 | B2 * | 5/2022 | Farrell ................. A61L 29/043 |
| 2004/0060260 | A1 | 4/2004 | Gottlieb et al. |
| 2005/0043715 | A1 * | 2/2005 | Nestenborg ......... A61M 25/002 |
| | | | 206/439 |
| 2009/0099531 | A1 | 4/2009 | Griesbach, III |
| 2013/0153446 | A1 | 6/2013 | Utas et al. |
| 2015/0265801 | A1 | 9/2015 | Rostami |
| 2015/0297861 | A1 | 10/2015 | Passalaqua et al. |
| 2016/0129219 | A1 | 5/2016 | Gustavsson et al. |
| 2017/0274176 | A1 | 9/2017 | Kelly et al. |
| 2017/0340857 | A1 | 11/2017 | Ryan et al. |
| 2018/0099117 | A1 | 4/2018 | Schonfeldt |
| 2018/0126035 | A1 | 5/2018 | O'Mahony et al. |
| 2020/0054795 | A1 * | 2/2020 | Farrell ..................... A61L 2/08 |

* cited by examiner

PACKAGED HYDROPHILIC MEDICAL PRODUCTS THAT ARE HYDRATED WITHIN THE PACKAGE AND METHODS OF MAKING THE SAME

The present application is the U.S. National Stage Application of PCT Application No. PCT/US2020/034036, filed May 21, 2020, which claims the benefit of and priority to U.S. Provisional Application No. 62/851,376, filed May 22, 2019, both of which are hereby incorporated herein by reference.

DESCRIPTION

Field of the Disclosure

The present disclosure generally relates to packaged hydrophilic medical devices that are hydrated within the package and methods of hydrating medical devices within the package. Even more particularly, the present disclosure relates to packaged hydrophilic catheter assemblies and methods of hydrating the same.

Background

One method of sterilization includes exposing an item or product to radiation to kill the microbes and sterilize the item/product. There are items/products wherein the conditions under which the radiation sterilization occurs can cause damage to the items/products. For example, there are certain items that are required to be radiation sterilized in dry or substantially dry conditions. If such items are radiation sterilized in a wet or hydrated condition, the exposure to radiation may lessen one or more qualities of the item or will damage the item. For example, some types of hydrophilic materials may become damaged by exposure to sterilizing radiation while the hydrophilic materials are in a hydrated state.

It is known to coat medical devices, such as urinary catheters, with a hydrophilic coating. When the hydrophilic coating is wetted or hydrated with a wetting fluid, such as water, it becomes extremely lubricous which eases introduction of the device into the body and aids in reducing pain and discomfort associated with such introduction.

In some applications, the hydrophilically coated medical device is provided in a "dry" state wherein the user is required to wet the hydrophilic coating with a wetting fluid immediately prior to insertion into the body. In other applications, it is desirable to provide a hydrophilically coated medical device that is in a ready-to-use condition right out of the package. In the field of urinary catheters, a hydrophilically coated catheter may be provided in a catheter package wherein the catheter is stored in the package in contact with water so that the hydrophilic coating is wetted within the package and the catheter is ready for use right out of the package.

For various reasons, including but not limited to efficiency, effectiveness and cost, it is desirable to radiation sterilize packaged medical device assemblies. In some instances, the hydrophilically coated medical device and water are placed in the package and the package is sealed. After the package is sealed, the package having the hydrophilically coated medical device and water therein is exposed to radiation, such as gamma or E-Beam radiation, to sterilize the medical device. It has been found, however, that sterilization of hydrophilic coatings in the hydrated state or while in contact with a wetting fluid can result in degradation of the coating or excessive crosslinking of the coating which can lead to an increase of coefficient of friction (decrease in lubricity) of the coating and/or cause instability of coating which may result in the coating undesirably detaching from the medical device prior to or during use.

Therefore, there remains a need for sterilized ready-to-use hydrophilic medical devices and methods of sterilizing and hydrating the hydrophilic medical devices.

SUMMARY

In one aspect, a packaged medical device product includes a package defining a cavity. The product also includes a hydrophilic medical device contained within the cavity and a container containing a hydration liquid within the cavity. The container is configured to open upon exposure to radiation, thereby releasing the liquid into the cavity.

In another aspect, a method of making a packaged medical device product includes placing a hydrophilic medical device in a cavity of a package and placing a liquid filled container within the cavity of the package. The liquid filled container is configured to open upon exposure to radiation. The package is closed and exposed to radiation, thereby opening the container.

DETAILED DESCRIPTION OF THE EMBODIMENTS

Figures 1, 2:
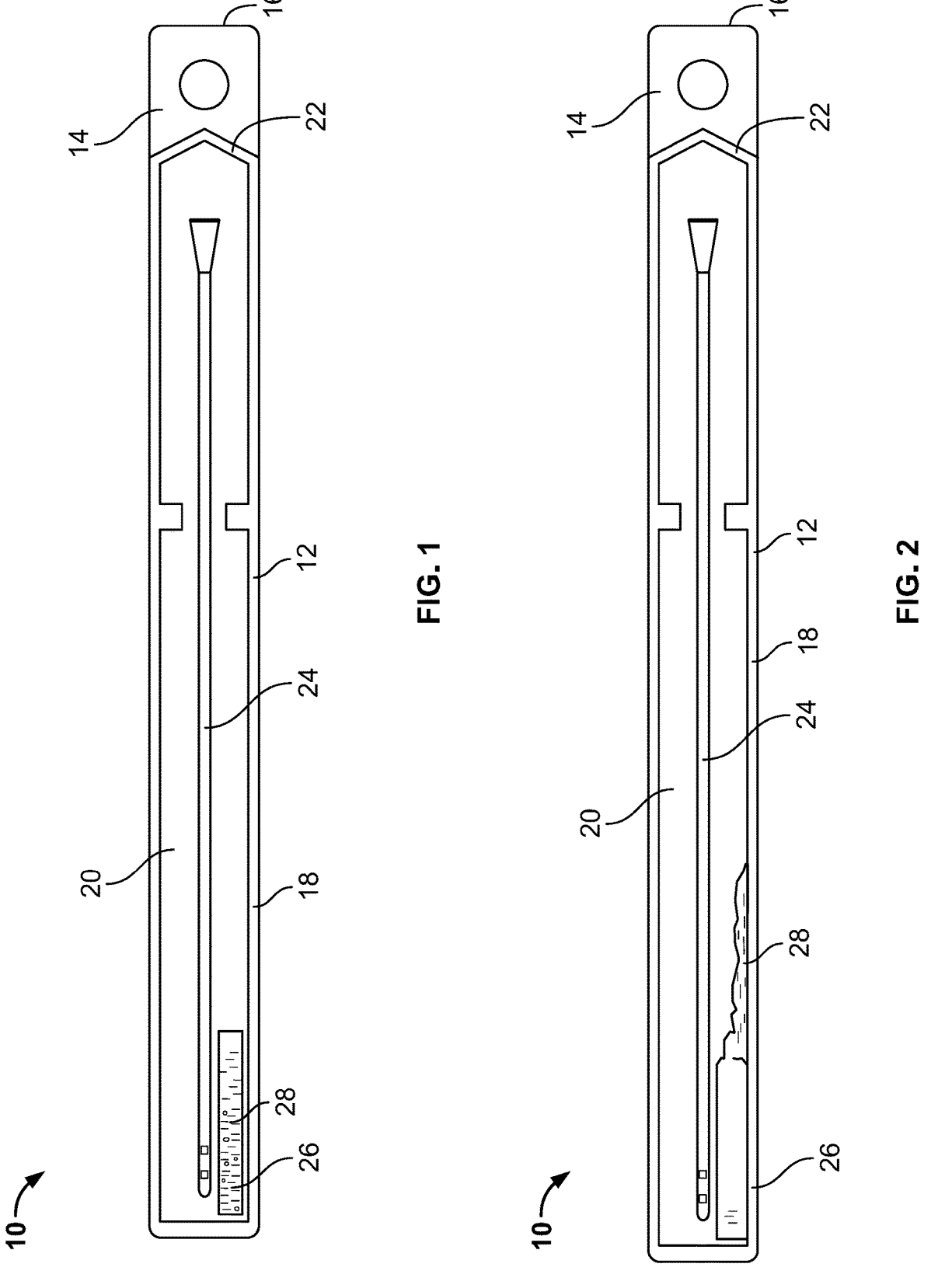
FIG. 1 is a top plan view of one embodiment of a packaged medical device product in accordance with the present disclosure.
FIG. 2 is a top plan view of the packaged medical device product of FIG. 1 shown with the container in an open condition.

The present disclosure is generally directed to packaged hydrophilic medical device products 10 that are ready to use right out of the package. Referring to FIGS. 1 and 2, the packaged hydrophilic medical device product 10 includes a sleeve, such as package 12 or a non-touch sleeve (not-shown) that surrounds that catheter and is used to grip the catheter for insertion. In the embodiment illustrated in FIGS. 1 and 2, the package 12 is formed from a front sheet 14 and back sheet 16 that are sealed together to form a peripheral seal 18 and define an internal cavity 20. At the top of the package 12, the front and back sheets 14 and 16 may be unattached above top seal 22. The package 12 may be opened by grasping these unattached portions and pulling the front sheet 14 and back sheet 16 away from each other to peal open the package 12 along seal 18. Optionally, the package 12 may be any other suitable package for containing a medical device. For example, the package may be a tear open package. Additionally, the material of the package, optionally, may be made from a gas impermeable material.

A hydrophilic medical device is contained within cavity 20. In the illustrated embodiment, the hydrophilic medical device is a hydrophilic catheter 24. The hydrophilic catheter 24 may be any suitable hydrophilic catheter that includes a hydrophilic outer surface that becomes lubricous when hydrated with a hydration medium, such as water. For example, the catheter 24 may include a lubricious hydrophilic coating on the outer surface of the catheter.

A container 26 of hydration liquid 28 also may be located within the cavity 20. The container 26 may be a sachet or pouch containing the hydration liquid 28. The container 26 is configured to open or burst upon exposure to radiation, thereby releasing the hydration liquid 28 into the cavity 20. The released liquid 28 comes into to contact with the hydrophilic material of the catheter 24 to hydrate the material, and thereby active the lubricous characteristics of the hydrophilic material.

The hydration liquid 28 may be any suitable hydration liquid, such as water or an aqueous solution. The hydration liquid 28 may also include any suitable additives. The hydration liquid 28 also includes a gas, such as carbon dioxide or nitrogen, dissolved in the liquid. Optionally, the hydration liquid 28 may be super saturated with the gas. During exposure to sterilizing radiation, such as e-beam or gamma sterilization, energy impinges on the materials of the product (e.g., package, container, liquid), resulting in heat generation. The container 26 containing the liquid 28 utilizes this heating phenomenon to burst the container 26 containing the liquid. In one embodiment, a container 26 contains carbonated water, which includes dissolved carbon dioxide gas. When the packaged product is exposed to radiation, the hydration liquid 28 heats up, thereby releasing the carbon dioxide gas. The released gas increases the pressure within the container 26, and this increased pressure causes the container to burst. The liquid 28 is then released from the burst container 26 into the cavity 20. Optionally, the liquid 28 may include a foaming agent, such as a surfactant. The surfactant may be, for example, sodium dodecyl sulphate or sodium methyl cocoyl taurate. When a foaming agent is included, the hydration liquid will foam upon opening of the container and release of gases from the hydration liquid.

The container 26 may be made form a liquid impermeable material, such a polymer/metal laminate. For example, the laminate may a sheet or film that includes layers of polyethylene and aluminum. Optionally, the container 26 may have a weak portion configured to burst due to the increase of gas pressure within the container. The weak portion may be a weak seal or a weakened portion of the container material. For example, the container material may be partially cut through some of the layers. For instance, the container material may include a layer cut through the top layers or bottom layers of the materials.

When the sleeve containing the catheter and container 26 is a no-touch sleeve, the sleeve may have an introducer at one end and may be attached to the funnel of the catheter.

It should be understood that various changes and modifications to the presently preferred embodiments described herein will be apparent to those skilled in the art. Such changes and modification can be made without departing from the spirit and scope of the invention disclosed herein.

What is claimed is:

1. A packaged medical product, comprising:
a package defining a cavity;
a hydrophilic medical device contained within the cavity; and
a sachet contained within the cavity; and
a hydration liquid within the sachet, the hydration liquid being supersaturated with a dissolved gas, wherein the sachet includes a weak portion configured to burst, and wherein upon exposure to sterilizing radiation, dissolved gas is released from the hydration liquid to increase pressure within the sachet, thereby bursting the weak portion of the sachet and releasing the hydration liquid from the sachet.

2. The packaged medical product of claim 1, wherein the sachet is configured to burst upon exposure to E-beam radiation.

3. The packaged medical product of claim 1, wherein the dissolved gas comprises at least one of carbon dioxide and nitrogen.

4. The packaged medical product of claim 1, wherein the weak portion comprises at least one of a weak seal and a partial cut in a material of the sachet.

5. The packaged medical product of claim 1, wherein the hydrophilic medical device comprises a urinary catheter.

6. The packaged medical product of claim 1, wherein the sachet is made from a liquid impermeable material.

7. The packaged medical product of claim 6, wherein the material comprises a polymer/metal laminate.

8. The packaged medical product of claim 1, wherein the hydration liquid contains a foaming agent.

9. A method of making a packaged medical product, comprising:
placing a hydrophilic medical device within a cavity of a package;
placing a liquid filled sachet within the cavity of the package, wherein the liquid filled sachet contains a hydration liquid and the hydration liquid includes a dissolved gas;
closing the package; and
exposing the package to radiation to heat the hydration liquid and release the dissolved gas from the hydration liquid, thereby increasing pressure within the sachet to burst the sachet and release the hydration liquid.

10. The method of claim 9, wherein exposing the package to radiation comprises exposing the package to E-Beam radiation.

11. The method of claim 9, wherein the dissolved gas comprises at least one of carbon dioxide and nitrogen.

12. The method of claim 9, wherein the hydration liquid is supersaturated with the dissolved gas.

13. The method of claim 9, wherein the sachet includes a weakened portion that is configured to open.

14. The method of claim 13, wherein the weakened portion comprises at least one of a weak seal and a partial cut in a material of the sachet.

15. The method of claim 9, wherein the hydrophilic medical device comprises a urinary catheter.

16. A packaged medical product, comprising:
a sleeve;
a hydrophilic medical device contained within the sleeve;
a sachet contained within the sleeve; and
a hydration liquid within the sachet, the hydration liquid being supersaturated with a dissolved gas, wherein the sachet includes a weak portion configured to burst, and wherein upon exposure to sterilizing radiation, dissolved gas is released from the hydration liquid to increase pressure within the sachet, thereby bursting the weak portion of the sachet and releasing the hydration liquid from the sachet.

17. The packaged medical product of claim 16, wherein the dissolved gas comprises at least one of carbon dioxide and nitrogen.

18. The packaged medical product of claim 16, wherein the weak portion comprises at least one of a weak seal and a partial cut in a material of the sachet.

19. The packaged medical product of claim 16, wherein the sachet is made from a liquid impermeable material.

20. The packaged medical product of claim 16, wherein the hydration liquid contains a foaming agent.

* * * * *